United States Patent [19]

Thompson et al.

[11] Patent Number: 5,624,808
[45] Date of Patent: Apr. 29, 1997

[54] METHOD FOR IDENTIFYING CELLS COMMITTED TO APOPTOSIS BY DETERMINING CELLULAR PHOSPHOTYROSINE CONTENT

[75] Inventors: Peter Thompson, Danville; Fridjtof Lund-Johannsen, Fremont, both of Calif.

[73] Assignee: Becton Dickinson and Company, Franklin Lakes, N.J.

[21] Appl. No.: 412,256

[22] Filed: Mar. 28, 1995

[51] Int. Cl.⁶ .................. G01N 33/53; G01N 33/536; G01N 33/574
[52] U.S. Cl. ............... 435/7.24; 435/7.1; 435/7.2; 435/7.23; 435/40.5; 435/40.51; 435/960; 435/968; 436/172; 436/175; 436/536; 436/800; 436/813; 436/824
[58] Field of Search .................. 435/7.24, 7.1, 435/7.2, 7.23, 40.5, 40.51, 960, 968; 436/536, 172, 175, 800, 813, 824

[56] References Cited

PUBLICATIONS

Farr, A.G. et al. Cell, vol. 43, No. 2, pt. 1, pp. 543–550 Dec. 1985.
Otani, H. et al., J. Biol. Chem., vol. 268, No. 30, pp., 22733–22736 Oct. 25, 1993.
Far, D.F. et al., Cytometry, vol. 15, No. 4, pp. 327–334 Apr. 1, 1994.
Yousefi, S. et al., Proc. Natl. Acad. Sci. USA, vol. 91, No. 23, pp. 10868–10872 Nov. 8, 1994.

*Primary Examiner*—Christopher L. Chin
*Assistant Examiner*—Scott F. Welch
*Attorney, Agent, or Firm*—Royal N. Ronning, Jr.

[57] ABSTRACT

A novel approach to study changes in protein tyrosine phosphorylation during apoptosis, and thereby identify cells committed to apoptosis is presented, methods used to study apoptosis and tyrosine phosphorylation at the single cell level are combined to study directly whether apoptosis in hematopoietic cells is associated with changes in cellular phosphotyrosine levels. The changes in cellular phosphotyrosine content strongly correlated with the appearance of features of cell death such as cell shrinkage, DNA fragmentation and loss of membrane integrity.

6 Claims, 18 Drawing Sheets

FIG-1A  UNFIXED THYMOCYTES
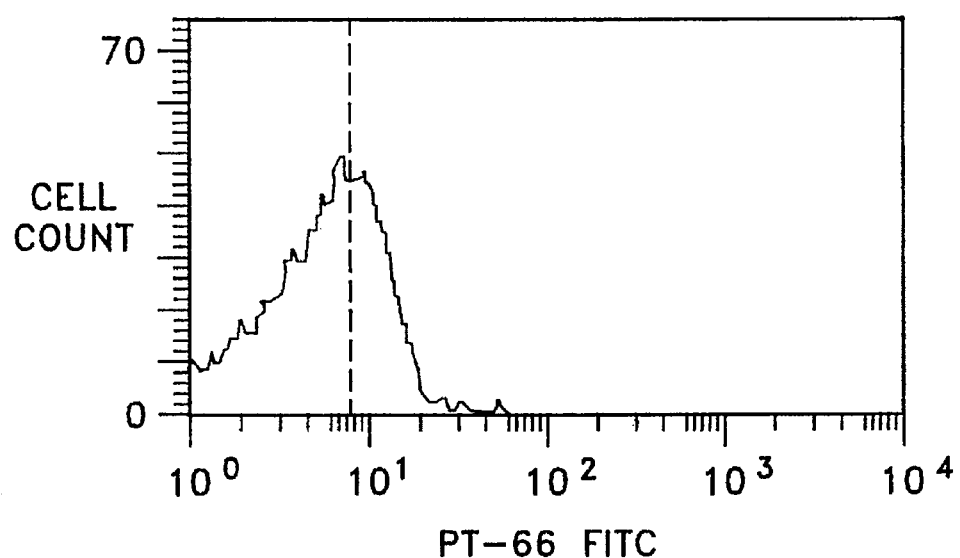
FIG-1B  FIXED AND PERMEABILIZED THYMOCYTES
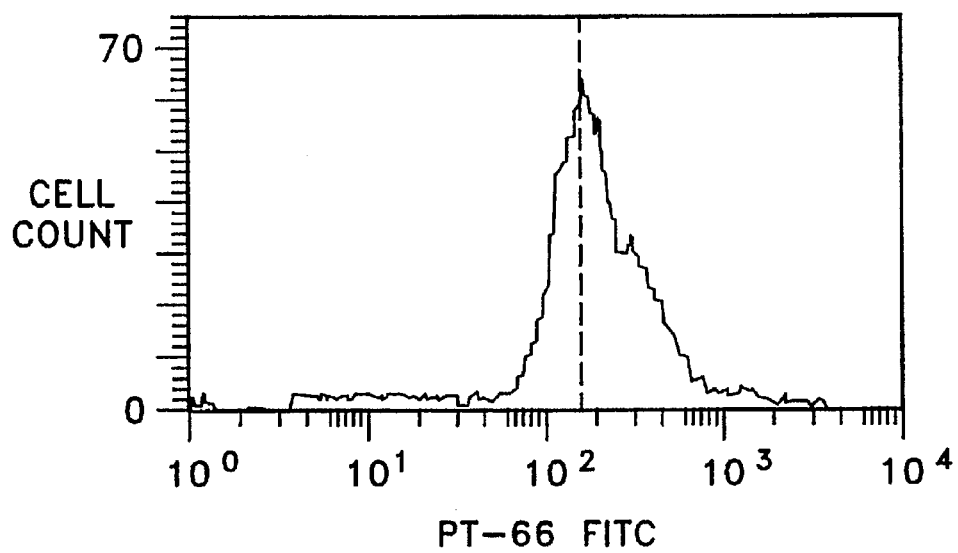

FIG-1C UNFIXED THYMOCYTES
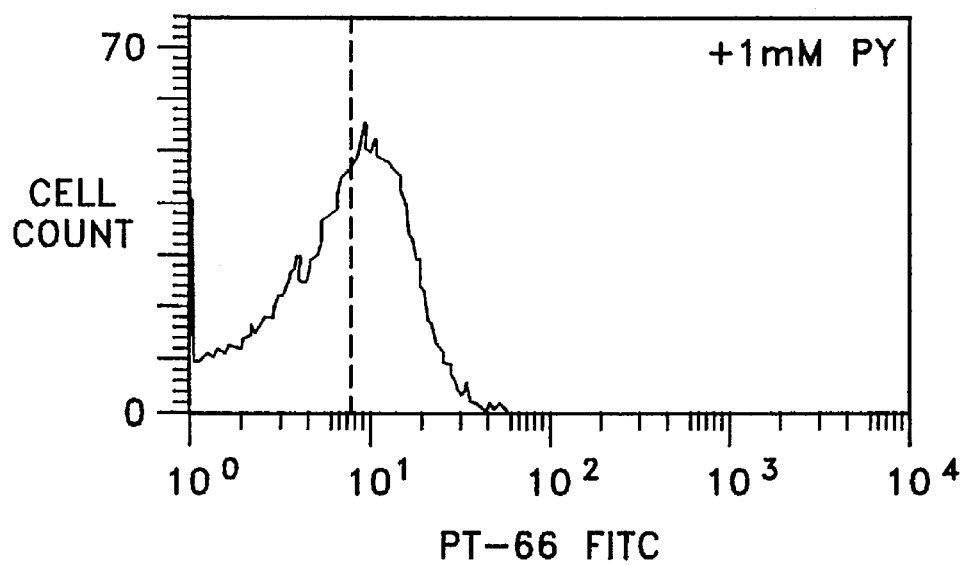
FIG-1D FIXED AND PERMEABILIZED THYMOCYTES
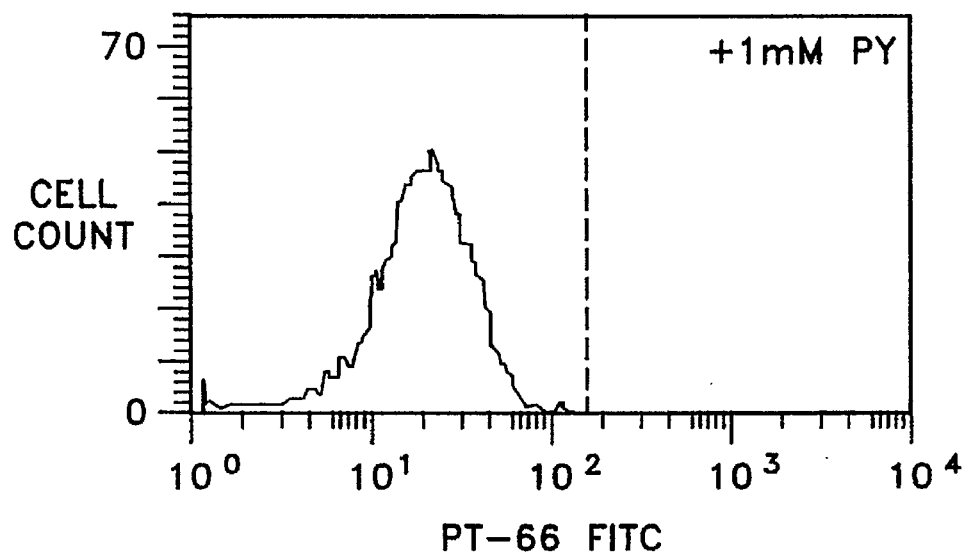

FIG-1E UNFIXED THYMOCYTES
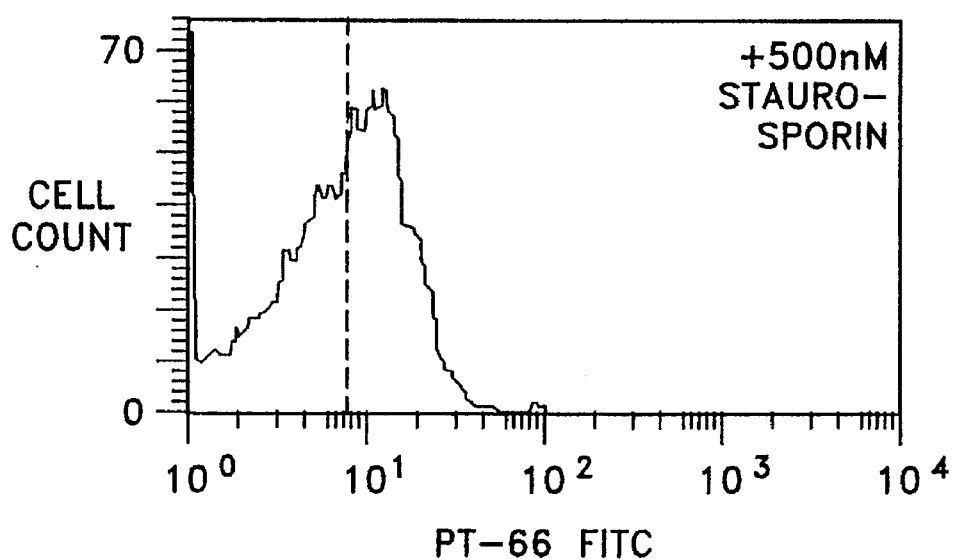
FIG-1F FIXED AND PERMEABILIZED THYMOCYTES
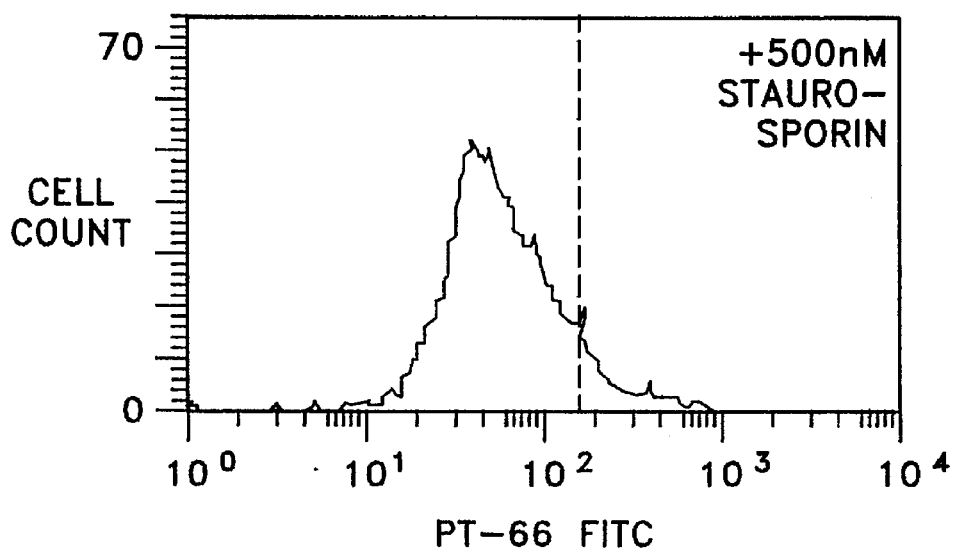

FIG-1G UNFIXED THYMOCYTES
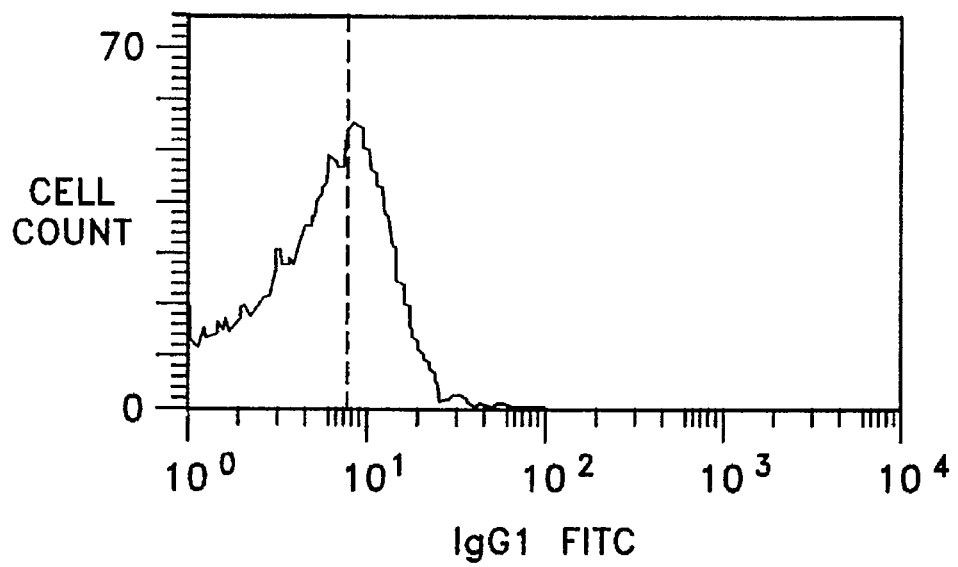
FIG-1H FIXED AND PERMEABILIZED THYMOCYTES
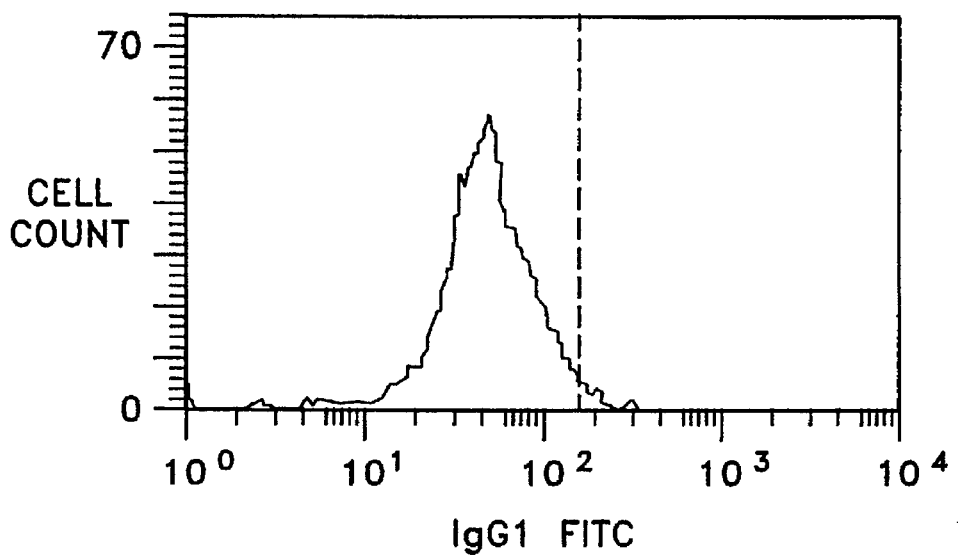

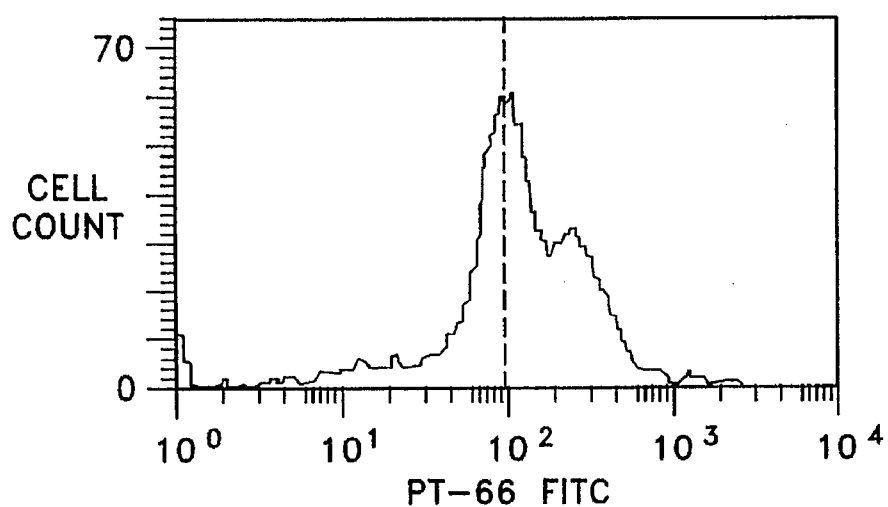
FIG-2A MEDIUM ONLY
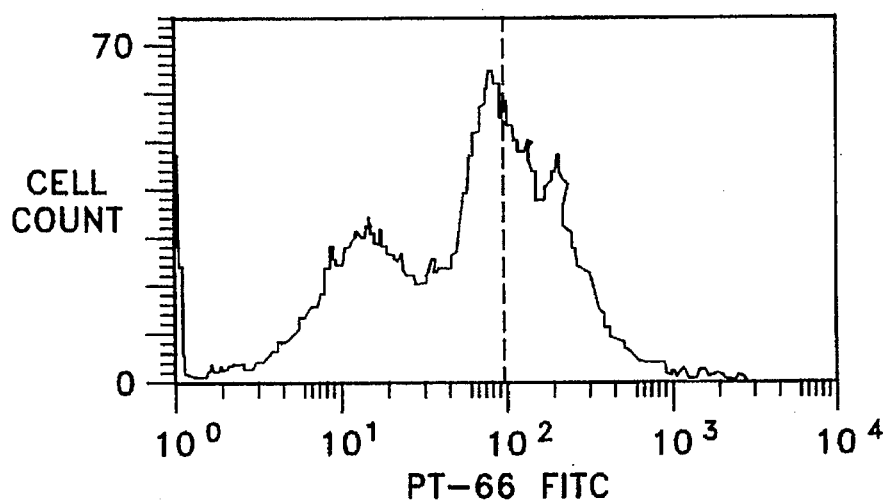
FIG-2B Dex 2.5h
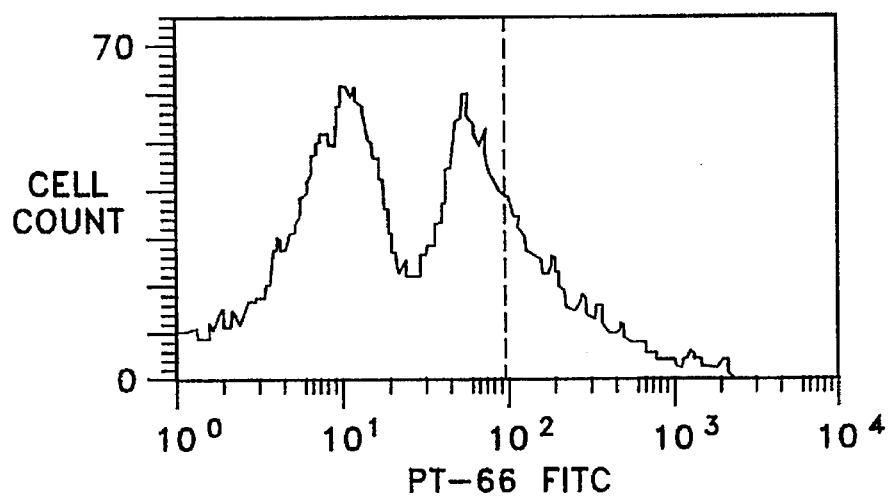
FIG-2C Dex 5.0h

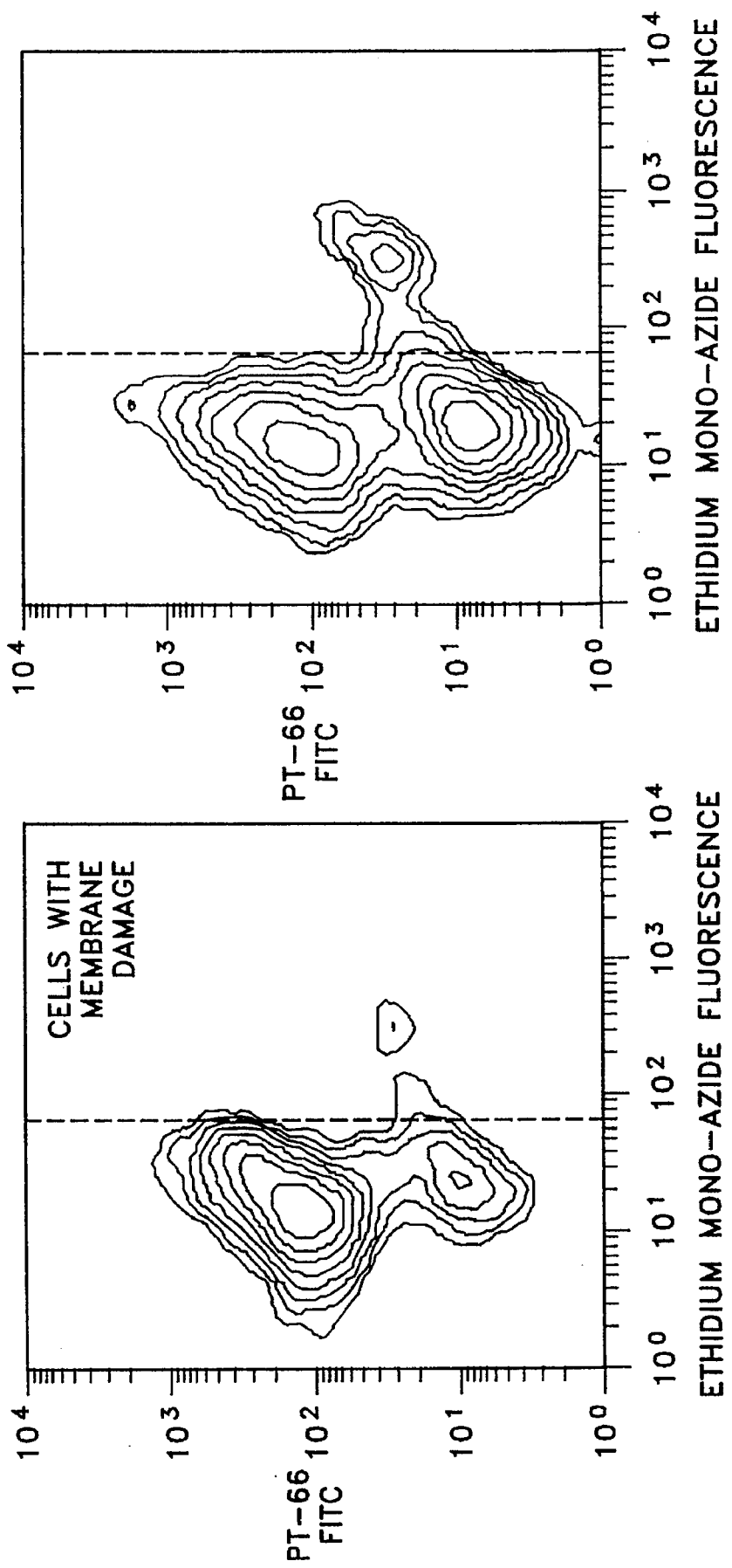

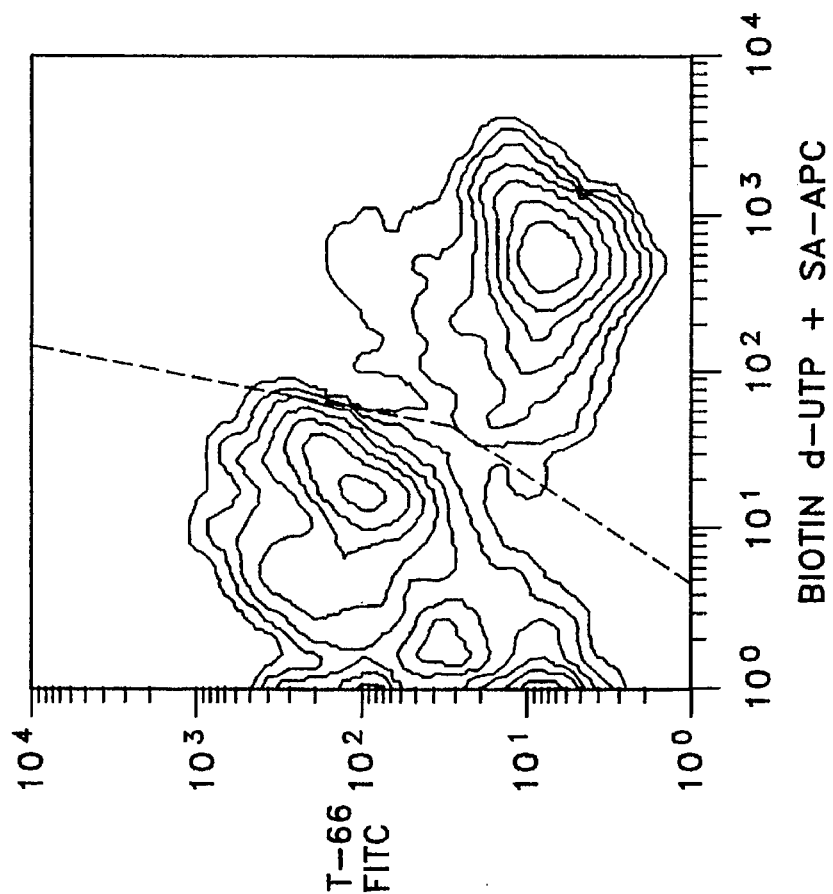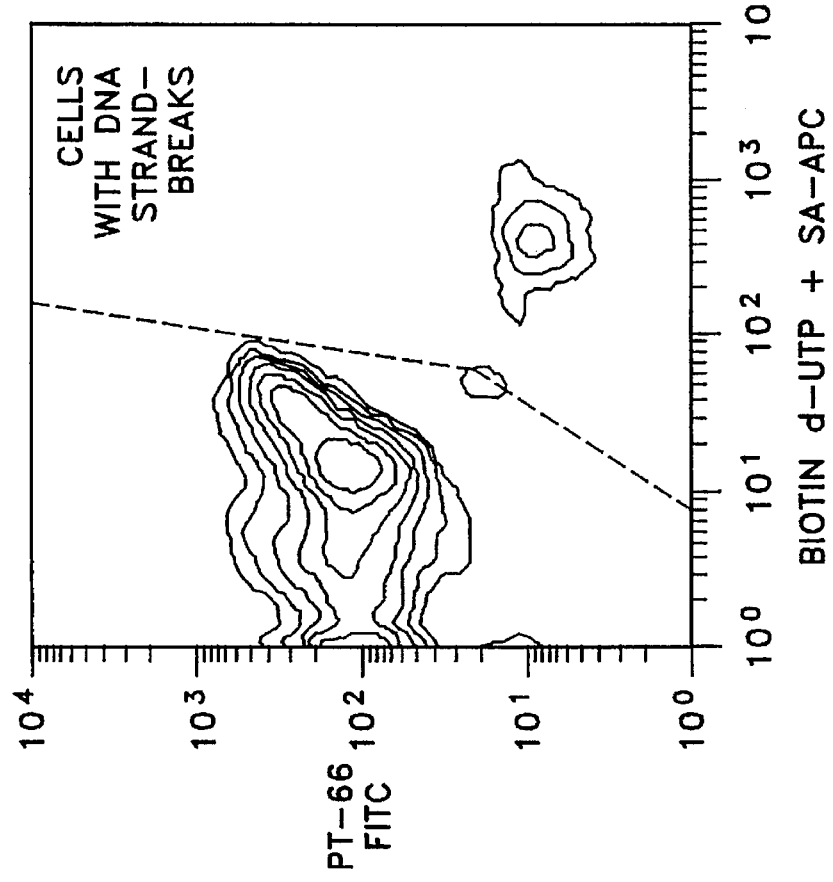

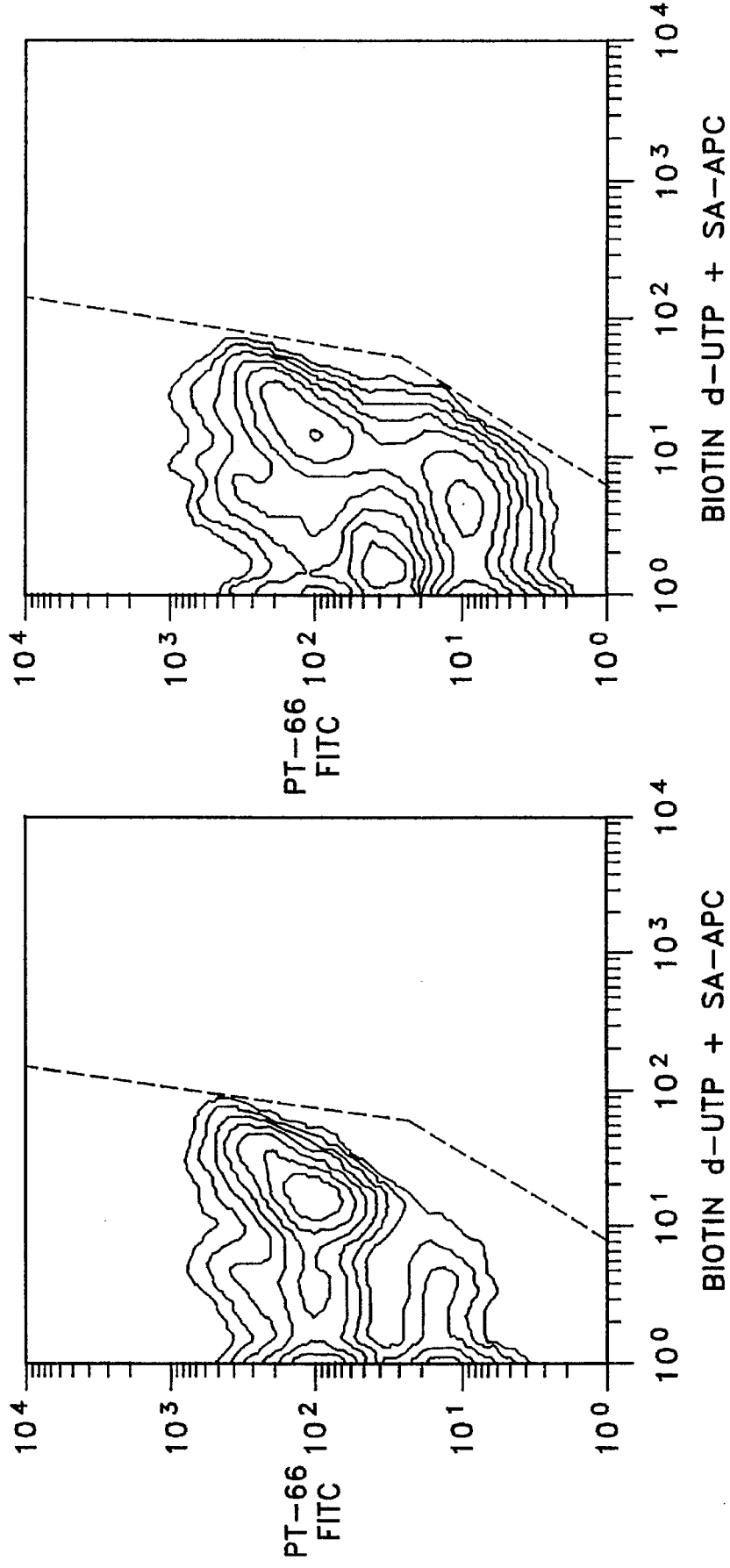

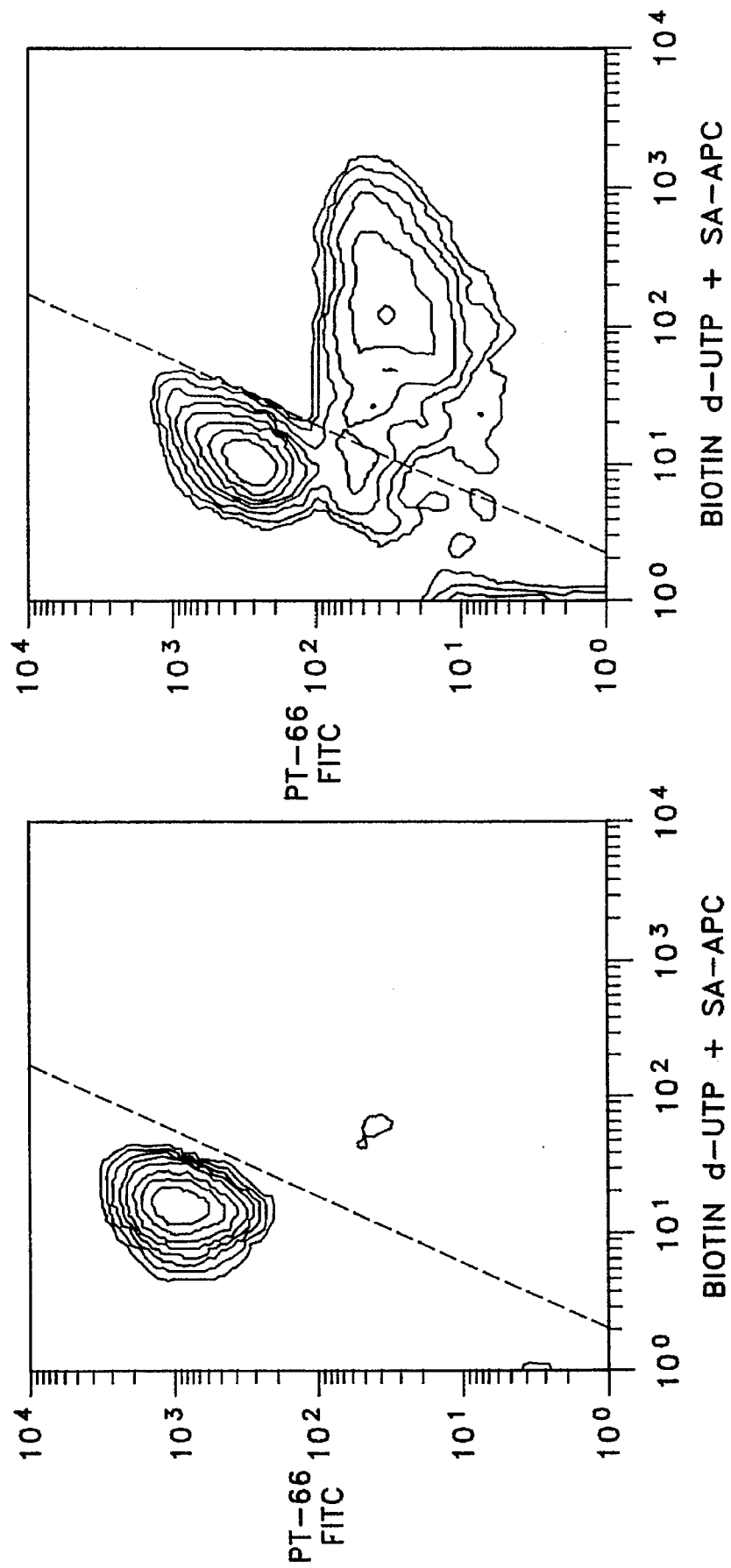

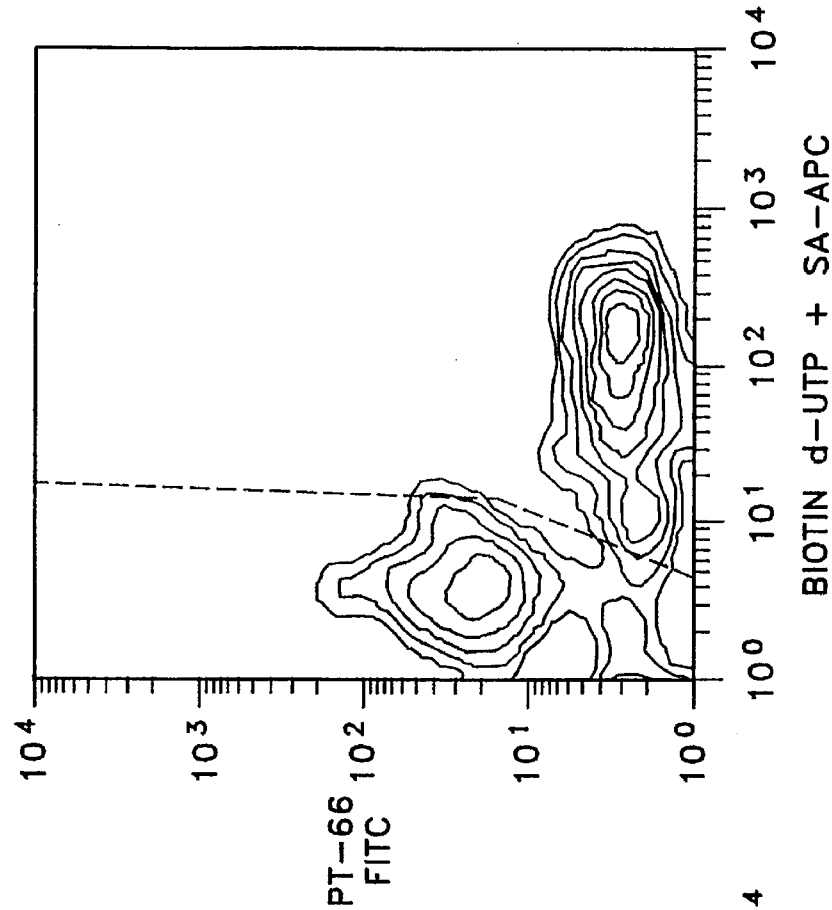
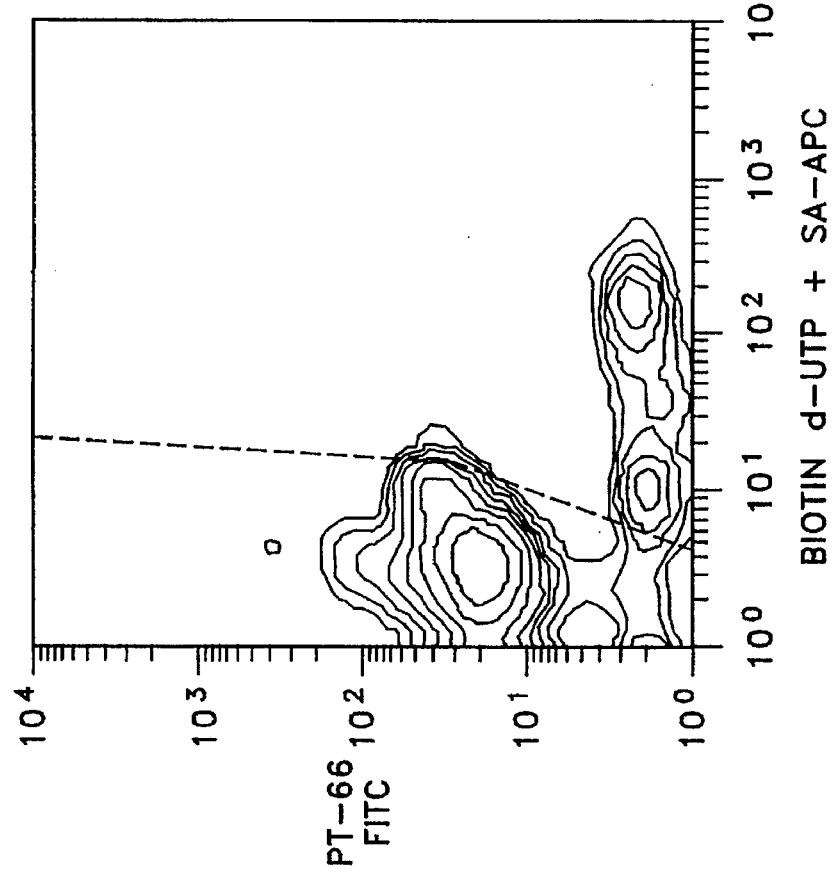

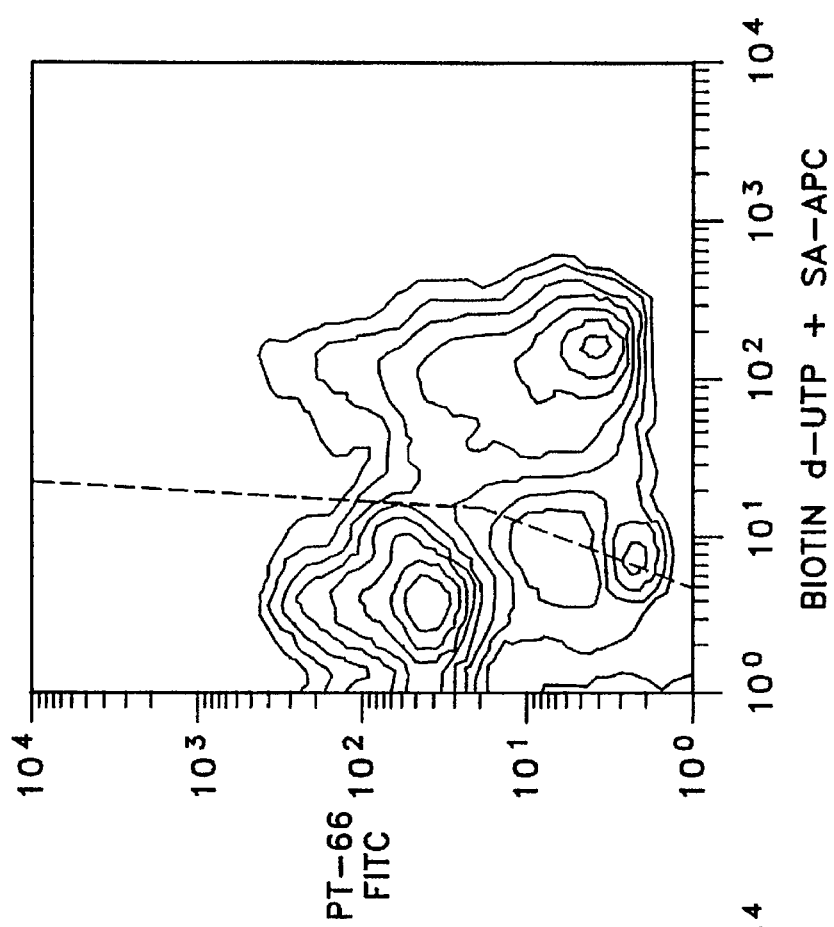
FIG-6D + DEXAMETHASONE
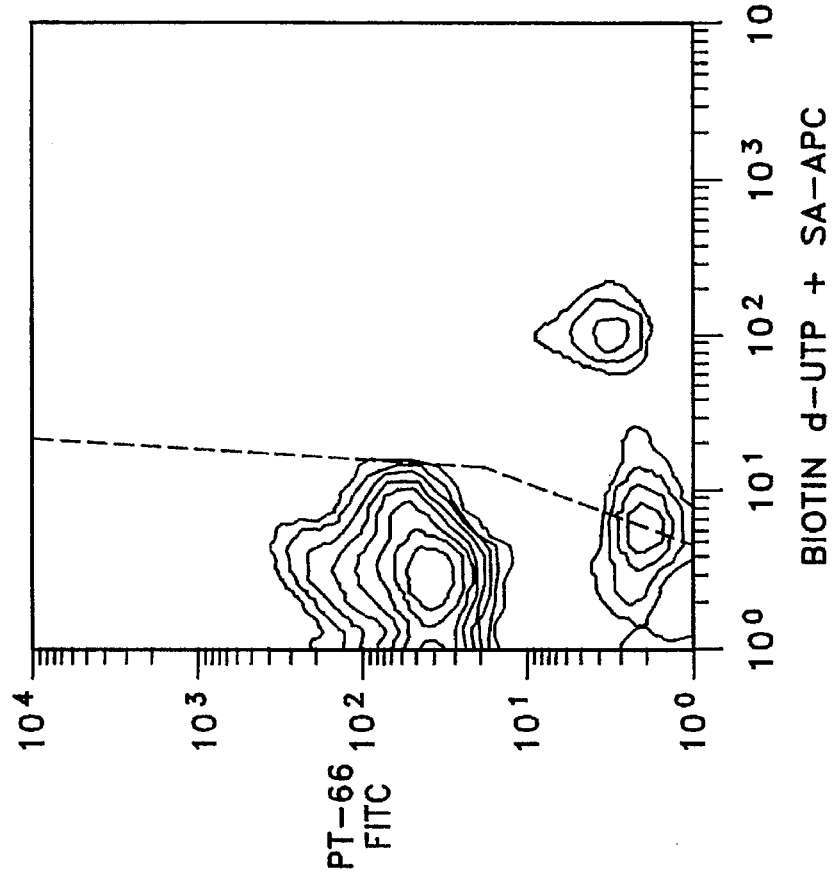
FIG-6C 15μM

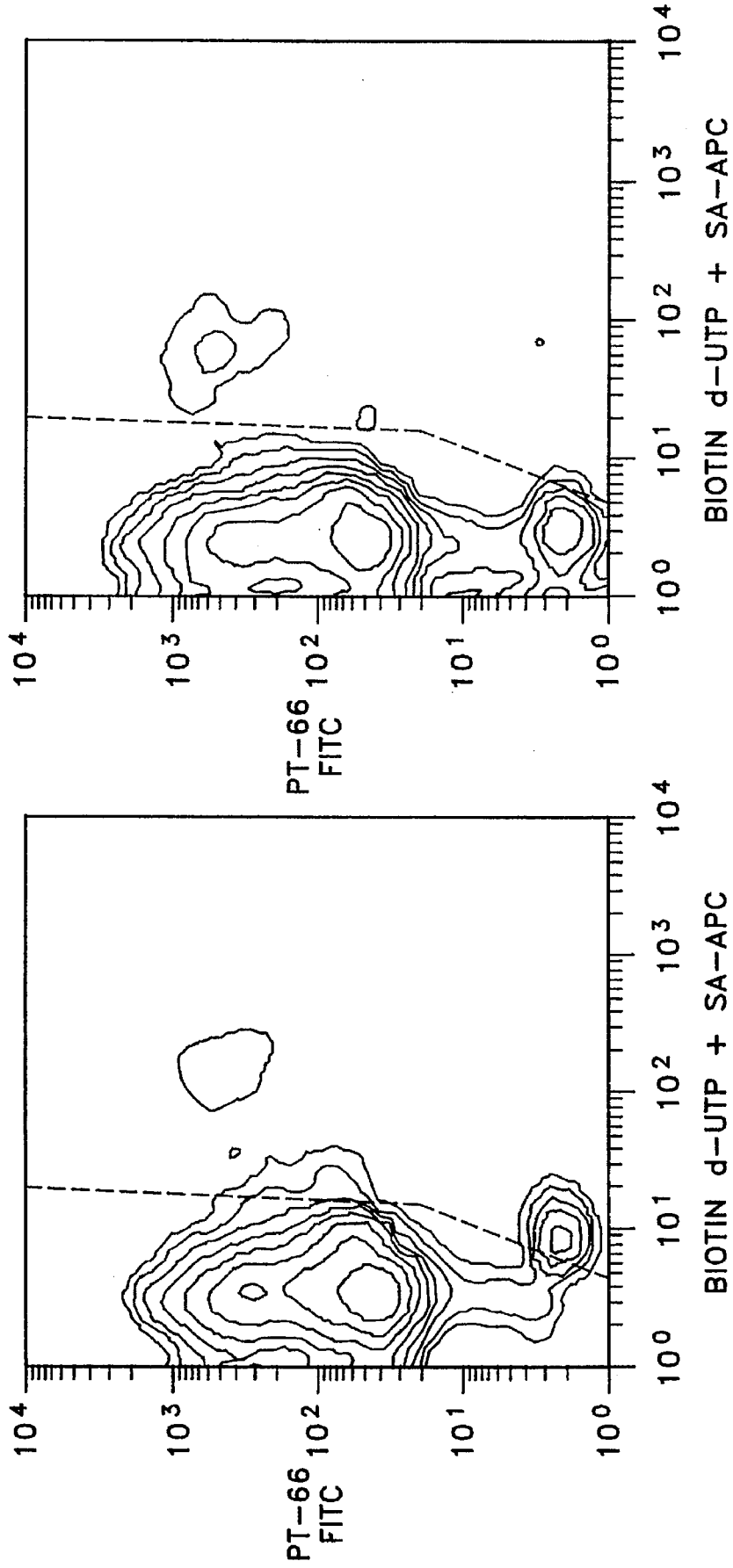

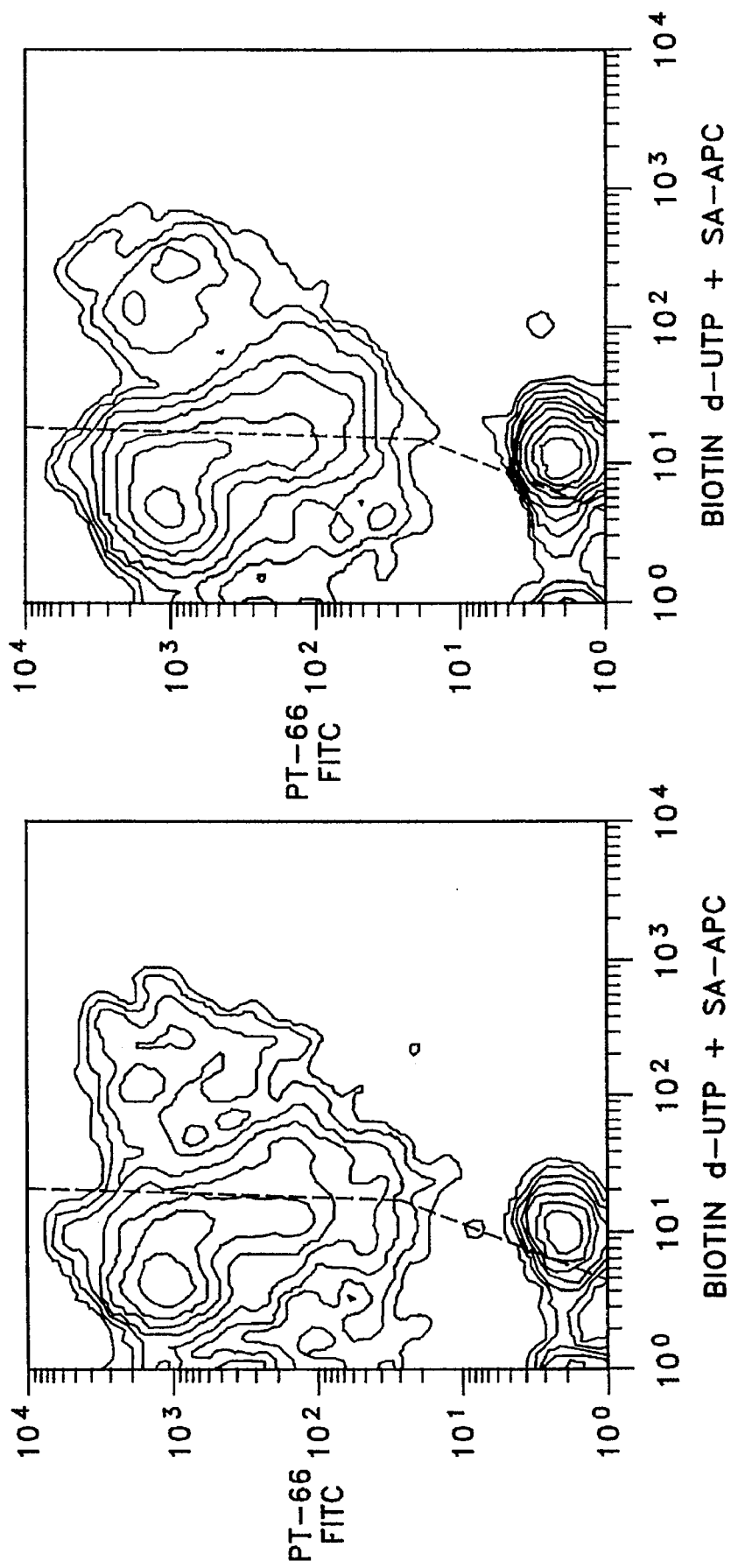

METHOD FOR IDENTIFYING CELLS COMMITTED TO APOPTOSIS BY DETERMINING CELLULAR PHOSPHOTYROSINE CONTENT

BACKGROUND OF INVENTION

The number of cells in multicellular organisms is kept in balance by proportionate cell growth and death. Although, cell growth has been most extensively studied, it has become increasingly clear that cell death is also carefully regulated. Thus, in the healthy organism most cells die as a result of the controlled activation of processes that break down cellular components. Well studied examples of such processes include internucleosomal fragmentation of DNA by endonucleases, and activation of selected protease. In addition to ensuring a balance in cell numbers, apoptosis is a major mechanism for eliminating potential harmful cells such as autoreactive lymphocytes and cells with DNA damage. This is clearly demonstrated in lpr/lpr mice where lack of the APO-1 receptor results in deficient apoptotic signaling and a failure to eliminate autoreactive lymphocytes. As a consequence the mice stiffer from antoimmune disease. Defective cell death is also an important factor in carcinogenesis. Results showing that successful anti-cancer therapy, including irradiation and many antineoplastic drags, induce apoptosis in cancer cells suggest that information about the mechanisms of cell death may be of value for designing therapy aiming to remove disease-causing cells.

Although certain features of apoptotic cells seem to reflect a final common pathway for physiologic cell death, the suicidal process is still poorly characterized. The intracellular signaling pathways that lead to activation of the lytic enzymes are also largely unknown. Tyrosine kinases and phosphatases are, however, likely to play important roles as dysregulated tyrosine kinases induce immortality and resistance to chemotherapy in certain cell types. This has been timber supported by studies showing effects of tyrosine kinase and phosphatase inhibitors on apoptosis, some of which indicate that these enzymes may be targets for phamcological manipulation of apoptosis. Most of the studies on regulation of tyrosine phosphorylation in apoptosis have, however, focused on immediate changes in tyrosine phosphorylation induced by apoptotic stimuli. Very little is known about changes in cellular phosphorylation status that occur later in the process when cells commit to apoptosis. Although important for understanding the effects inhibitors and stimulators of tyrosine phosphorylation, such downstream phenomena, that occur over long time periods, are difficult to study as apoptosis in a cell population is rarely synchronized. Any sample may therefore contain cells at different stages in the process thereby complicating the analysis of data obtained by analysis of whole cell suspensions.

SUMMARY OF INVENTION

This invention presents a novel approach to study changes in protein tyrosine phosphorylation during apoptosis, and thereby identify cells committed to apoptosis. Methods to study apoptosis and tyrosine phosphorylation at the single cell level are combined to study directly whether apoptosis in hematopoietic cells is associated with changes in cellular phosphotyrosine levels. The changes in cellular phosphotyrosine content strongly correlated with the appearance of features of cell death such as cell shrinkage, DNA fragmentation and loss of membrane integrity were measured directly at the single cell level, signaled by a dramatic decrease in cellular phosphotyrosine levels. These results suggest that extensive tyrosine-dephosphorylation is an intrinsic part of the apoptotic process of hematopoietic cells and may be mechanistically linked to the induction of cell death.

BRIEF DESCRIPTION OF THE FIGURES

FIG. 1 depicts staining of murine thymocytes with the anti-phosphotyrosine antibody PT-66 (panels A–F) and isotype control (G–H). Left panels shows staining of unfixed cells. Right panels show cells that were stained after fixation and permeabilization as described in The dotted lines in the left and right panels indicate the peak channel for the PY staining of unfixed and permeabilized cells, respectively. Panels C–D shows the staining in the presence of 1 mM soluble phosphotyrosine. Panels E–F show cells that were preincubated for 30 min at 37C with 500 nM staurosporin prior to the staining. The results are representative of four experiments.

FIG. 2 depicts the effect of dexamethasone on thymocyte PY levels. Murine thymocytes were incubated 5 h in medium only (tipper panel), 2.5 h in medium followed by 2.5 h in medium containing 0.1 µM dexamethasone (middle panel) or 5 h in medium containing 0. µM dexamethasone (lower panel). The cells were then permeabilized and stained with anti-PY The dotted line indicates the peak channel of the PY staining of cells that were incubated with medium only.

FIG. 3 depicts the combined determination of cell membrane integrity and cellular phosphotyrosine content. Thymocytes were incubated for 5 h in medium with or without 0.1 µM dexamethasone. The cells were then stained with ethidium monoazide, permeabilized and stained with anti-phosphotyrosine. Cells considered having increased ethidium monoazide staining and thus membrane defects are to the right of the dotted line. The results are representative of four experiments.

FIG. 4 depicts the combined determination of DNA strand breakage and decreased phosphotyrosine concentration cells with DNA strand breaks are to the right of the dotted line.

FIG. 6 depicts correlated measurement of cellular PY-levels and the extent of DNA-strand breaks in various cell types undergoing apoptosis. Combined staining for measurement of cellular PY levels and DNA strand breaks was performed A–B: HL-60 cells incubated for 4 h in the absence (A) or presence (B) of . . . M camphotecin. C–D: Wehi cells incubated for 24 h in the absence (C) or presence of 10 µg/ml anti-mouse IgM.E–F: Raji cells cultured for 48 h in medium with 10% (E) or 1% fetal bovine serum. The results are representative of four experiments.

DETAILED DESCRIPTION OF THE INVENTION

Figure 5A:
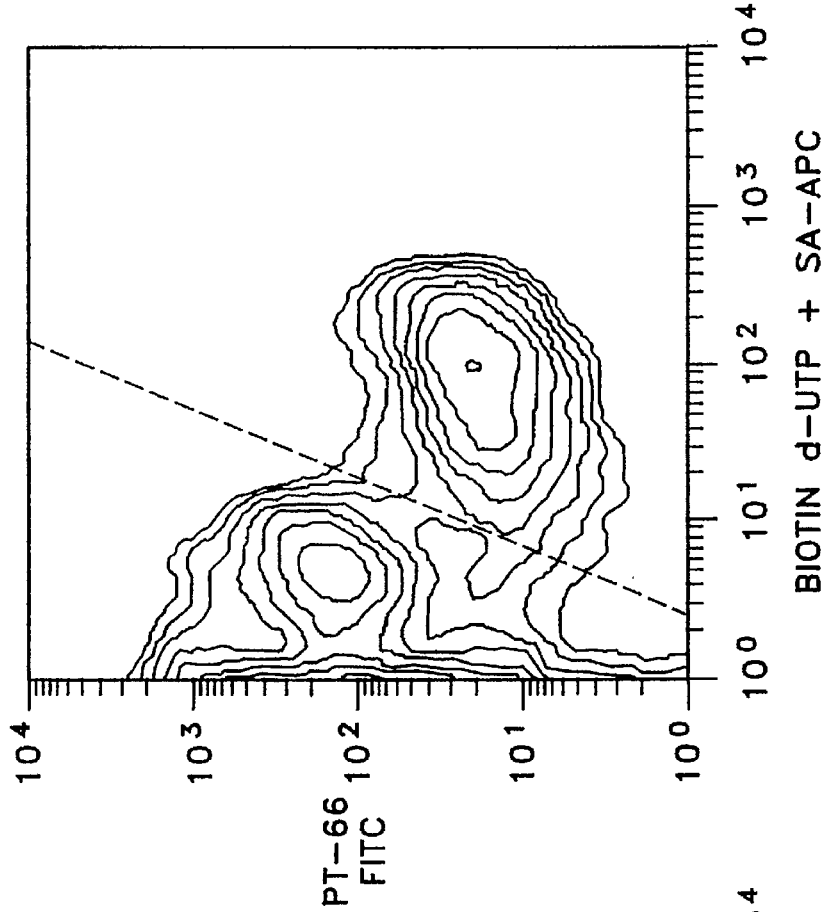
FIG. 5 depicts combined determination of DNA strand breaks and cellular phosphotyrosine content. Thymocytes were incubated for 5 h in medium with (B, D)or without (A,C) 0.1 µM dexamethasone. Combined staining of phosphotyrosine and DNA strand breaks was performed. A and B shows cells that were stained in the presence of terminal deoxynucleotidyl transferase. C and D shows the background staining in samples where the enzyme was omitted from the reaction mixture. Cells with higher staining in the presence of terminal transferase are to the right of the dotted line and considered to have DNA strand breaks. The events were gaited on ethidium monoazide$^{dim}$ cells (see FIG. 3). The results are representative of four experiments.
Figure 5B:
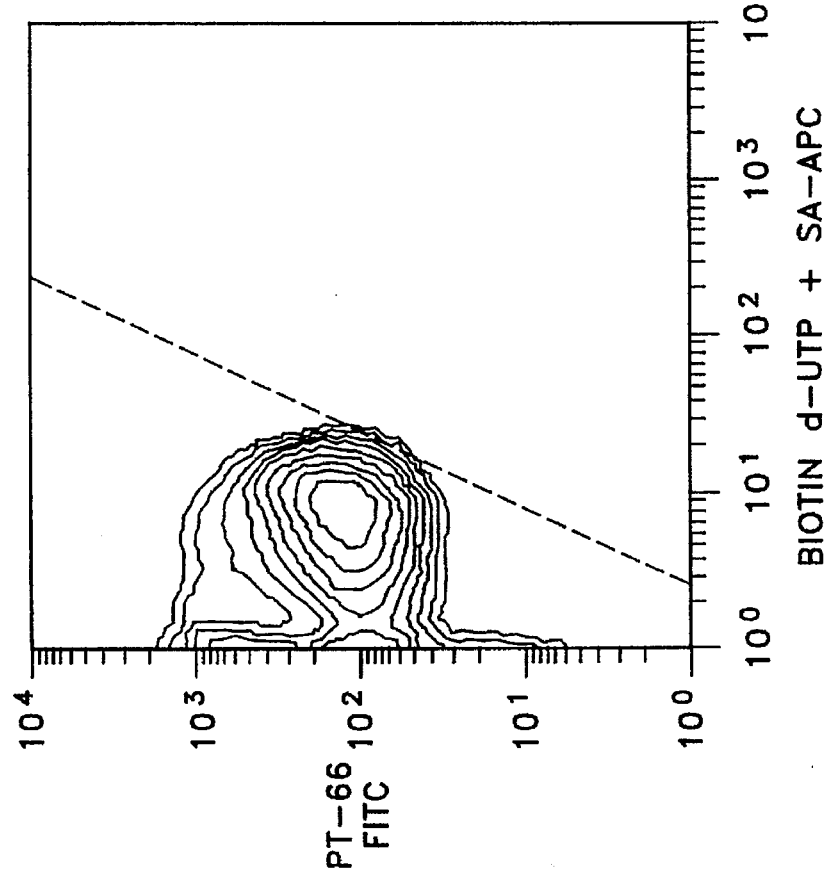

The identification of a cell committed to apoptosis can be determined by the measurement of cellular phosphotyrosine content. It has been observed that the apoptosis of cells, including hematopoietic cells, is preceded by and associated with decreases in phosphotyrosine, with the degree of reduction roughly correlating with the likelihood of the cell to apoptosis.

Thus, by monitoring the phosphotyrosine content of cells in a sample, the proportion of cells in that sample committed to apoptosis can be determined. If a random sample of cells in a population is selected, this in turn, can be used to predict the proportion of cells in that population which are committed to undergo apoptosis, providing a valuable tool for use in studies of cell death.

The phosphotyrosine content can be measured by any convenient method which provides quantitative results, including immunostaining and analysis in suspension or histologic sections; it is preferably accomplished by immunostaining of permeabilized cells and analysis by flow cytometry. In a preferred embodiment, the permeabilized cells are stained with an antibody specific for phosphotyrosine conjugated to fluorosceinisothicyanate (FITC).

The measurements can then be compared against the concentration of phosphotyrosine in normal (i.e., cells not committed to apoptosis) cells (the "normal physiological level") and any reduction in concentration below this level is indicative of likelihood of apoptosis

EXAMPLE

1. Reagents

Staurosporine (Sigma) was kept at −20° C. 1 mM in dimethylformamide. NaVO4 (1 M in $H_2O$, kept at −20° C. $H_2O$ (kept at 4° C). Catalase (Sigma cat. #C10) was kept at −20° C. and dissolved in PBS immediately before use. Saponin (Sigma cat. #. S2149), phosphotyrosine were dissolved in PBS. Ethidium monoazide (Molecular Probes) was kept at 1 mg/ml in ethanol at −20° C. and diluted 1:1000 in PBS immediately before use. Pervanadate was prepared fresh every day by mixing $NaVO_4$ with a 30 fold molar excess of $H_2O_2$. After 5 rain residual $H_2O_2$ removed by diluting the mixture 1:10 in PBS containing 1 mg/ml catalase. The solution was kept on ice until used.

2. Antibodies

PT66-FITC (mlgG1 anti-phosphotyrosine ) was obtained from Sigma and, PY20 (mlgG2anti-phosphotyrosine) was obtained from Transduction gaboratories. The monoclonal anti-phosphotyrosine antibody PY20 was kindly conjugated to FITC and R-Phycoerythrin by Quadrat Nasrati and Bamy Abrams at Becton Dickinson Immunocytometry Systems (BDIS). Streptavidin Allophycocyanin was frown BDIS.

3. Cells

Mouse thymocytes were prepared by mechanical disruption of a freshly excised thymus. Thymocytes were washed, resuspended in 50 mL of prewarmed (37° C.) median with $5×10^{-5}M$ 2-mercaptoethanol, and plated in the wells of a 24-well tissue culture plate at 2 mL/well. Dexamethasone (Sigma Chemical Co., St. Louis, Mo.) was used at 0.1 µM. Raji cells, HL-60 cells and unless specified all cell lines were kept in RPMI containing 10% FCS, 1 mM glutamine and 1 mM sodium pyruvate.

4. Staining of intracellular phosphotyrosine

Intracellular phosphotyrosine was detected by suspending. Cells suspended at $1-5×10^6$/ml in PBS containing 1% fetal bovine serum (PBS-FCS) and mixing with an equal volume of PBS containing 2 mM EDTA, 2 mM $NaVO_4$ and 0.1% saponin. Following 10 min of incubation in a water bath holding 20°–22° C., 4 ml PBS-FCS was added, the cells centrifuged and the supernatant discarded. The cells were then stained on ice with fluorochrome-conjugated anti-phosphotyrosine mAb. In some experiments, 1 mM soluble phosphotyrosine was added to the cells prior to the anti-PY mAb to evaluate the level of non-specific staining (see figures). Immunostained cells were either run immediately or resuspended in 0.5% paraformaldehyde and kept at 4° C. until analysis or further treatment for analysis of strand breaks.

5. Determination of cell membrane integrity using ethidium monoazide

In some experiments, the covalently binding non-vital DNA dye ethidium monoazide was used to stain cells with increased membrane permeability prior to fixation and permeabilization. Cells ($10^7$/ml) were suspended in PBS-FCS containing 2 µg/ml ethidium monoazide. The samples were placed under a fluorescent lamp for 15 minutes to allow photoaffinity binding of ethidium monoazide to DNA. After two washes in PBS-FCS, the cells were stained with anti-phosphotyrosine as described above. Cells with increased cell membrane permeability were detected as ethidium$^{bright}$ cells (see figures).

6. Detection of DNA -stand breaks by the in situ terminal deoxynucleotide transferase assay DNA strand breaks in single cells were detected by staining cells with ethidium monoazide and anti-phosphotyrosine antibodies as described above and fixed for at least 12h at 4C in 0.5% paraformaldehyde to stabilize the binding of the mAb. The cells were then washed once in PBS FCS. Buffers for terminal deoxy transferase (TDT) were prepared using a kit from Boehringer Mannheim (Cat. no. 220 582). To each sample 20 µl of a buffer was added consisting of 0.5 µl TDT solution (stock 25U/µl), 1 µl CoCl2 solution (stock 25 mM), 4 µl 5×TDT buffer, and 14.5 µl H2O. In addition, 0.5 µl biotin-16-dUTP (Stock 50 mM), Boehringer Mannheim cat. no. 1093 070) was added to each sample before incubation in a water bath holding 37° C. for 30 min. The cells were then washed twice in PBS FCS and stained on ice with streptavidin allophycocyanin (SA-APC) (BDIS). In all experiments, the TDT was omitted from at least one sample to evaluate non-specific binding of biotin-16-dUTP and SAAPC (see figures). Cells that had specifically incorporated biotin-16-dUTP in the presence of TDT were considered to have DNA strand breaks.

7. Single cell measurement of phosphotyrosine content

In order to measure phosphotyrosine content on a single cell level a flow cytometric technique was developed using a monoclonal antibody (mAb) specific for phosphotyrosine, PT-66, which was directly conjugated to FITC (APY-FITC). Data in FIGS. 1 and 2 demonstrate that the assay provides a valid measure of intracellular phosphotyrosine content. Staining of permeabilized cells with APY-FITC yielded significantly higher cellular fluorescence than that seen with a FITC-conjugated isotype control mAb (FIGS. 1B, 1H), staining of permeabilized cells with APY-FITC blocked by pre-incubation with excess phosphotyrosine (FIGS. 1B, 1D), or APY-FITC staining of non-permeabilized cells (FIGS. 1A, 1B). Incubation of murine thymocytes with the potent kinase inhibitor staurosporin results in a reduction of fluorescence intensity of permeabilized cells stained with APY- FITC to background levels (FIGS. 1B, 1H), but was without effect on APY-FITC staining of non-permeabilized cells (FIGS. 1A, 1E). Additional confirmation of assay specificity was provided by Western blotting of whole cell extracts prepared from murine thymocytes treated as in FIGS. 1B and 1D with a different mAb to phosphotyrosine. Finally, a separate mAb specific for phosphotyrosine, PY20, conjugated directly to FITC or phycoerythrin, yielded results similar to that demonstrated with PT66-FITC.

Comparing densitometric scans of the bands in the blots shown in FIGS. 2A and 2B suggests that the one log decrease in APY-FITC fluorescence intensity noted with staurosporin treatment (FIGS. 1B, 1F) of these cells represents a decrease in cellular phosphotyrosine content. These results also suggest that maintenance of the basal levels of cellular phosphotyrosine content in these cells requires active protein tyrosine phosphorylation.

8. Corticosteroid-induced apoptosis in thymocytes is associated with a dramatic decrease in cellular phosphotyrosine content To investigate whether induction of apoptosis leads to changes in cellular phosphotyrosine levels, corticosteroid-induced apoptosis in murine thymocytes was chosen as an initial model system. Freshly isolated thymocytes were cultured in the presence or absence of the corticosteroid dexamethasone and assayed for cellular phosphotyrosine content at selected time points. Dexamethasone-treated cultures demonstrated a time-dependent accumulation of cells with dramatically lowered cellular phosphotyrosine content indistinguishable from background (FIG. 2). The relative paucity of cellular events between the discrete phosphotyrosine$^{low}$ cell population and the phosphotyrosine$^{high}$ population in FIG. 3B argues for rapid kinetics for transit from the phosphotyrosine$^{high}$ population to the phosphotyrosine$^{low}$ cell population. Confirmation that these results did not represent an interference of dexamethasone with our assay system was afforded by parallel Western blots.

Compromise of the plasma membrane, demonstrable by vital dye staining, is a late event in apoptosis. As there are potent soluble protein tyrosine phosphatases, a trivial explanation for our results could be that the reductions in cellular phosphotyrosine content follow membrane permeabilization and protein leakage. In order to examine this directly, use was made of ethiduim monoazide (EMA), a cell impermeable nucleic acid dye which can be covalently cross-linked to its targets upon photoactivation of the azide group. Simultaneous evaluation of EMA staining and cellular phosphotyrosine content revealed that the decrease in cellular phosphotyrosine content demonstrated in FIG. 3B precedes and is independent of apoptosis-induced alterations in membrane permeability (FIG. 3).

Endonuclease-mediated cleavage of cellular DNA is a common observation in apoptosis, though the extent of DNA fragmentation varies across model systems, and is thought to represent a common endpoint in the execution of apoptotic programs. In situ end-labeling of cleaved DNA with labeled nucleotides, mediated by TdT, and detection of cells thus labeled by flow cytometry is a sensitive assay for endonuclease activity. In order to more precisely define the relationship between the accumulation of DNA strand breaks and the observed decrease in cellular phosphotyrosine content, the two parameters were simultaneously measured in the thymocyte system. The data from these experiments revealed that DNA strand breakage and decreased cellular phosphotyrosine content were effectively coincident (FIGS. 4A, 4B) in thymocytes. In other model systems, however, tyrosine dephosphorylation seemed to precede DNA fragmentation. Thus apoptosis, defined by the demonstration of DNA strand breaks, induced in murine thymocytes by corticosteroid treatment is associated with a dramatic decline in cellular phosphotyrosine content.

Figure 5F:
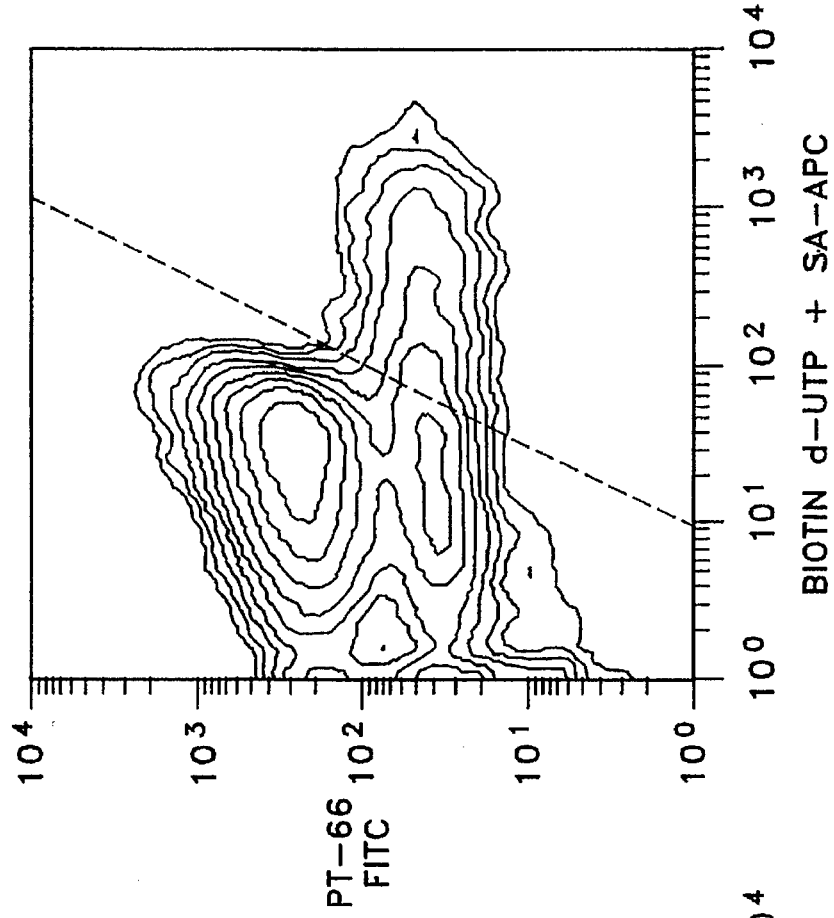
Figure 5E:
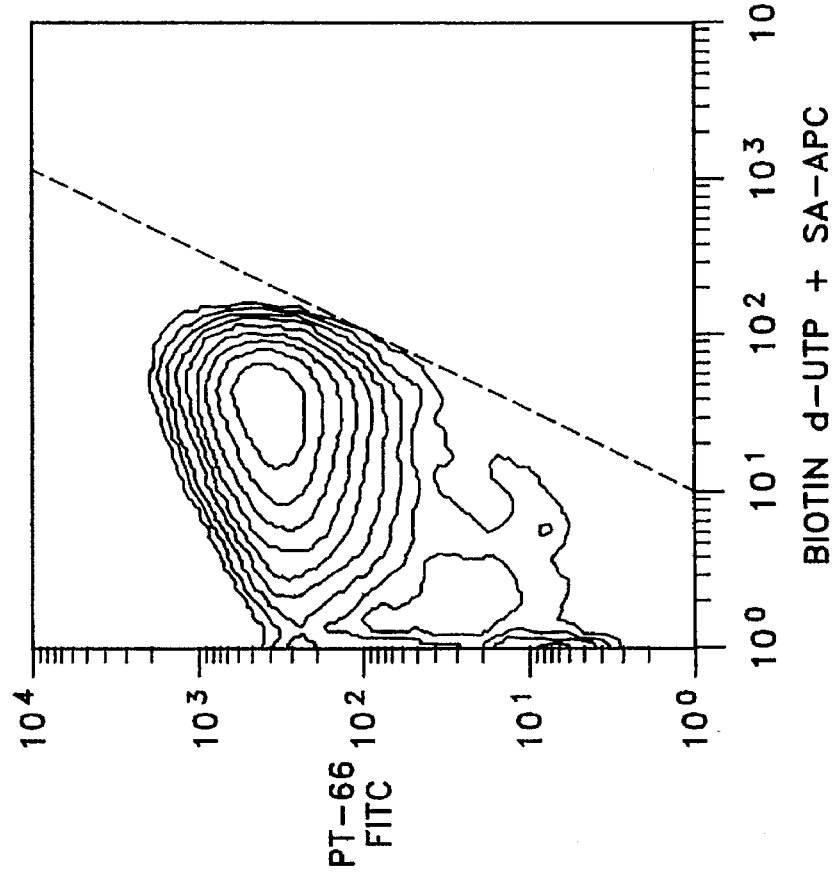

9. Dramatic reductions in cellular phosphotyrosine content are commonly observed during apoptosis To examine whether decreased phosphotyrosine content during apoptosis is peculiar to the thymocyte model or reflects a general characteristic of cells undergoing apoptosis, we measured cellular phosphotyrosine content and DNA fragmentation in three additional different models of apoptosis in hematopoietic cells (FIG. 5). These included campothecin treatment of HL-60 cells, in engagement of WEHI cells with anti-mouse IgM, and scram starvation of Raji cells. In all cases, induction of apoptosis was associated with the appearance of a phosphotyrosine$^{low}$ cell population (FIG. 5). Intriguingly, in all of these models there is an accumulation of phosphotyrosine$^{low}$ cells with no discernible DNA strand breaks upon apoptosis induction. This is most clearly seen in the Raji model system (FIGS. 5E, 5F). These cells had the lowered forward angle light scatter characteristics of apoptotic B lymphoid cells. The data in FIG. 5 suggested that dramatic reductions in cellular phosphotyrosine content are a common feature of apoptosis and either temporally precede, or are mechanistically independent of, endonuclease-mediated DNA cleavage.

Figure 7A:
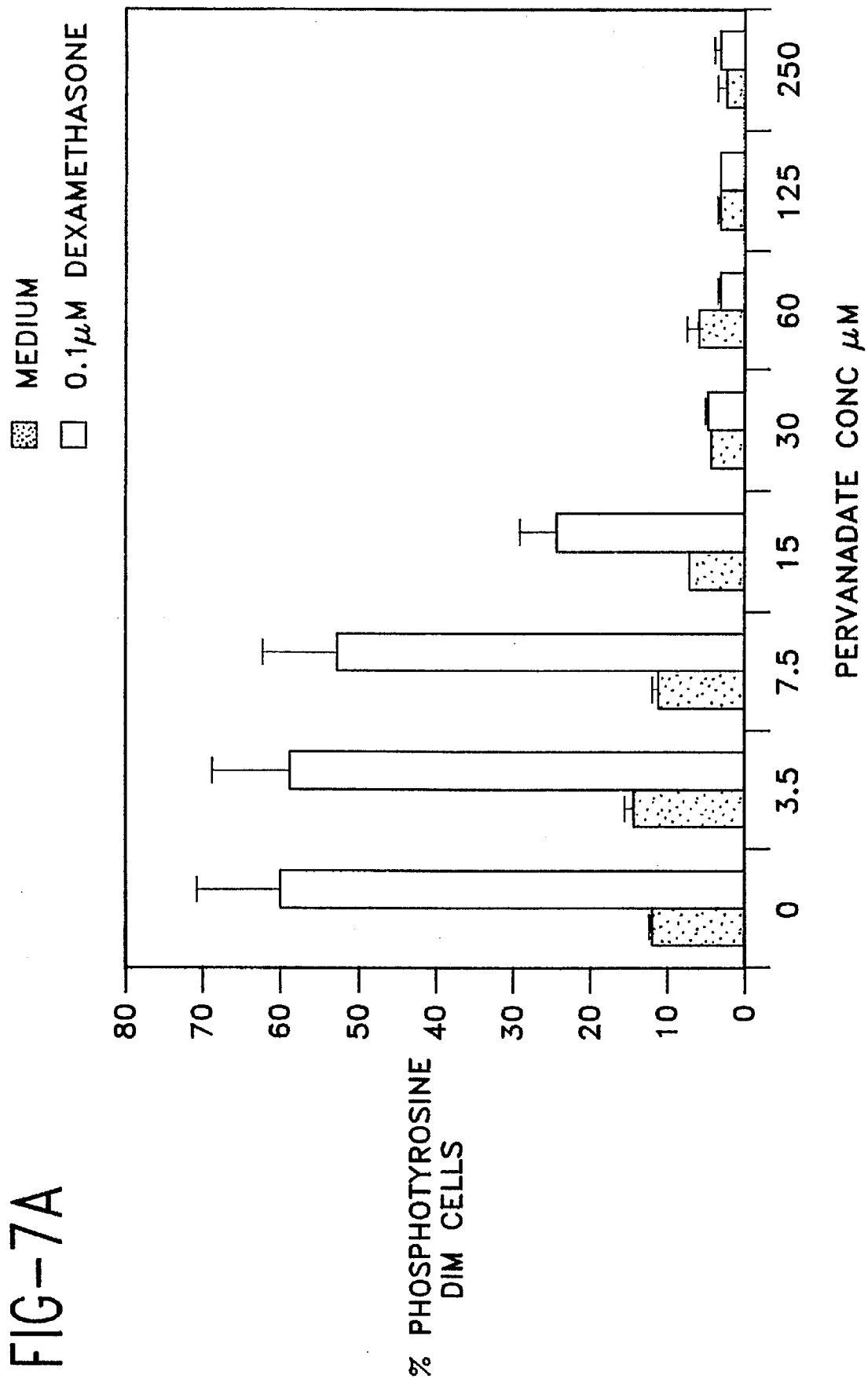
FIG. 7 graphically depicts the correlation of DNA strand breaks with phosphotyrosine content.
Figure 7B:
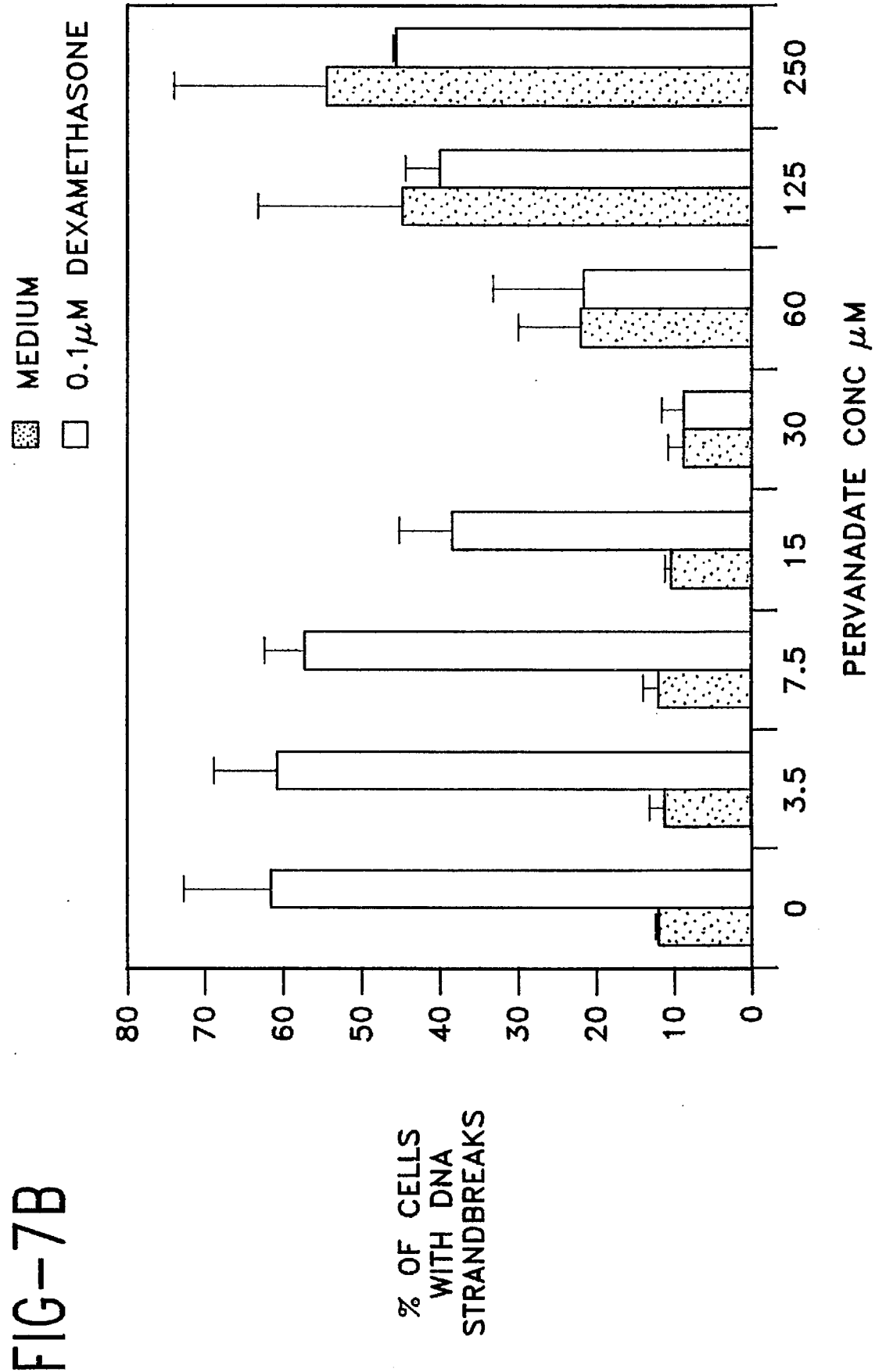
Figure 8:
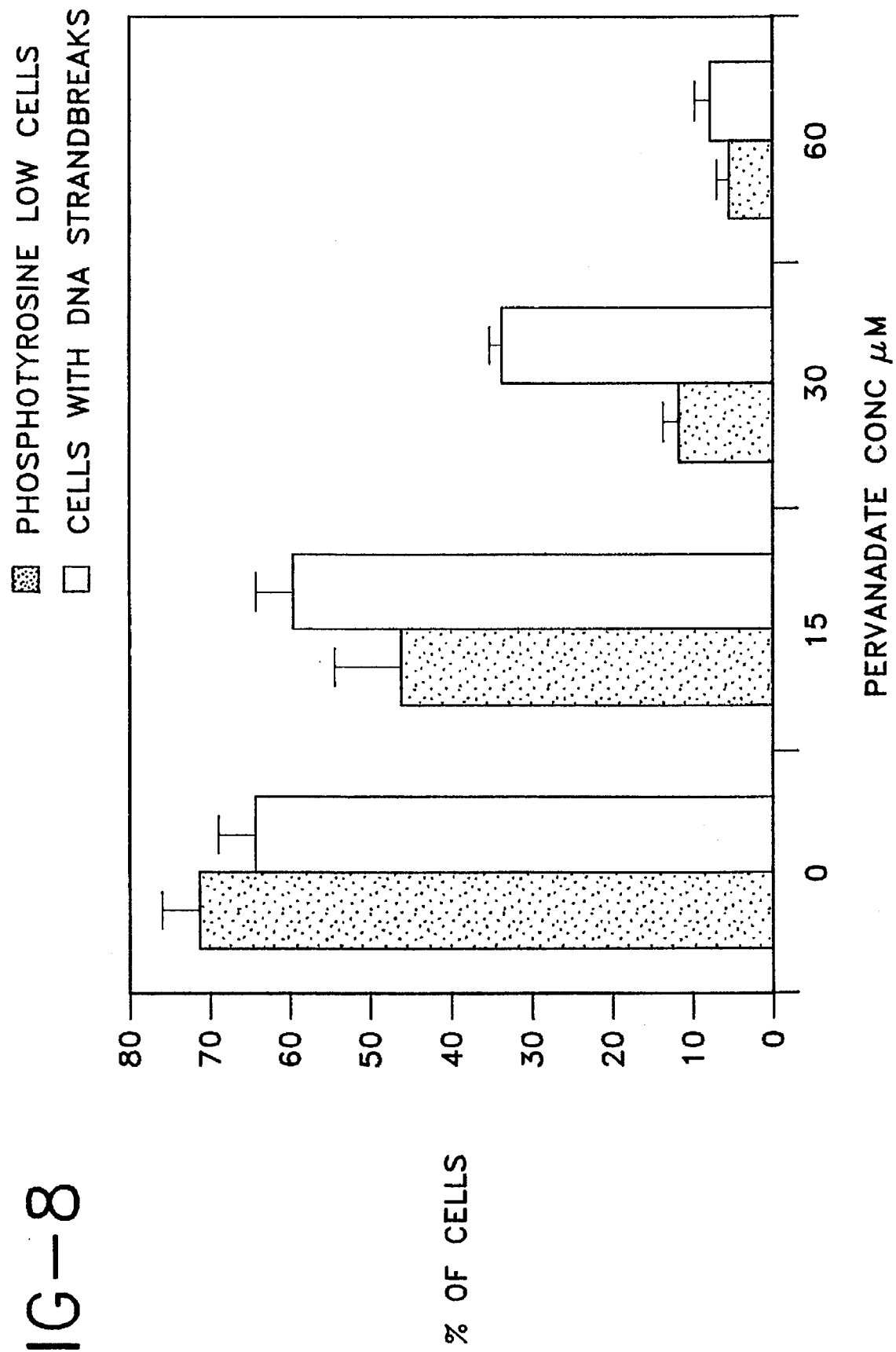
FIG. 8 graphically depicts the correlation of phosphtyrosine content with DNA strand breaks.

10. Dose-dependent inhibition of apoptosis by a protein tyrosine phosphatase inhibitor To evaluate whether tyrosine dephosphorylation was functionally linked to apoptosis, thymocytes were incubated with dexamethasone or etoposide in the presence of varying concentrations of the protein tyrosine phosphatase inhibitor pervanadate. The data from these experiments demonstrate dose-dependent inhibition apoptosis in both models, defined by the demonstration of DNA strand breaks (FIGS. 6A, 6C), decreased staining with LDS-751, or lowered forward angle scatter. The concentration of pervanadate which yielded the greatest inhibition of apoptosis was the lowest concentration that inhibited dephosphorylation. This concentration varied between 30–90 µM between the experiments, possibly due to the unstable nature of the compound. These data suggest that apoptosis induced by dexamethasone or etoposide requires protein tyrosine dephosphorylation, either for the commitment of cells to undergo apoptosis or for execution of apoptotic programs leading to DNA strand breakage. Higher concentrations of pervanadate resulted in DNA strand breakage in untreated control thymocytes to a similar extent seen in the dexamethasone- or etoposide-treated thymocytes (FIG. 7). Under these conditions dramatic decreases in cellular phosphotyrosine content were no longer evident (FIG. 7, FIG. 8), strongly suggesting that, at least under these conditions, the accumulation of DNA strand breaks is independent of decreases in cellular phosphotyrosine content.

It is apparent that many modifications and variations of this invention as hereinabove set forth may be made without departing from the spirit and scope thereof. The specific embodiments are given by way of example only and the invention is limited only by the terms of the appended claims.

What is claimed is:

1. A method for identifying which cells in a population of cells are committed to apoptosis by determining phosphotyrosine content of sample cells from said population wherein cells with concentrations of phosphotyrosine below normal physiological levels are classed as cells committed to apoptosis, while cells having phosphotyrosine concentrations at or near normal physiological are classed as cells not committed to undergo apoptosis.

2. The method of claim 1 wherein the phosphotyrosine content is determined by immunostaining of phosphotyrosine in permeabilized cells.

3. The method of claim 2 wherein the permeabilized cells are immunostained with an antibody conjugated to fluorescein isothiocyanate.

4. The method of claim 2 which further comprises analyzing said immunostained cells by flow cytometry.

5. The method of claim 2 wherein the immunostained cells are analyzed in suspension.

6. The method of claim 2, wherein immunostained cells are examined in the histologic sections.

* * * * *